(12) United States Patent
Avila et al.

(10) Patent No.: US 6,649,816 B2
(45) Date of Patent: Nov. 18, 2003

(54) *LACTUCA SATIVA* CULTIVAR, 'THERMO COS', EXHIBITING RESISTANCE TO LETTUCE DROP (*SCLEROTINIA MINOR*) AND TIPBURN

(75) Inventors: Tony M. Avila, Salinas, CA (US); Adolfo S. Mederos, Salinas, CA (US)

(73) Assignee: Central Valley Seeds, Inc., Salinas, CA (US)

( * ) Notice: Subject to any disclaimer, the term of this patent is extended or adjusted under 35 U.S.C. 154(b) by 65 days.

(21) Appl. No.: 09/811,254

(22) Filed: Mar. 15, 2001

(65) Prior Publication Data

US 2003/0018996 A1 Jan. 23, 2003

(51) Int. Cl.$^7$ .................. A01H 5/00; A01H 5/10; A01H 1/00
(52) U.S. Cl. .......... 800/305; 800/260; 800/298; 800/265
(58) Field of Search ............... 800/305, 260, 800/265, 298

(56) References Cited

U.S. PATENT DOCUMENTS 5,523,520 A * 6/1996 Hunsperger et al. ........ 435/410
5,684,226 A * 11/1997 Sarreal ...................... 800/200

OTHER PUBLICATIONS

Eshed et al. 1996. Less–than–additive epistatic interactions of quantitative trait loci in tomato. Genetics 143:1807–1817.*

Kraft et al. 2000. Linkage disequilibrium and fingerprinting in sugar beet. Theor. Appl. Genet. 101;323–326.*

* cited by examiner

*Primary Examiner*—David T. Fox
*Assistant Examiner*—David H Kruse
(74) *Attorney, Agent, or Firm*—Jondle & Associates PC

(57) ABSTRACT

Disclosed herein is the present invention which relates to a new distinct romaine (Cos) *Lactuca sativa* cultivar designated 'Thermo Cos', which exhibits resistance to lettuce drop and tipburn, a leaf color of Value 4 Chroma 4 Hue 7.5 GY according to the Munsell Color Chart for Plant Tissues.

7 Claims, 1 Drawing Sheet

Figure 1. The Pedigree of Lettuce Cultivar 'Thermo Cos'
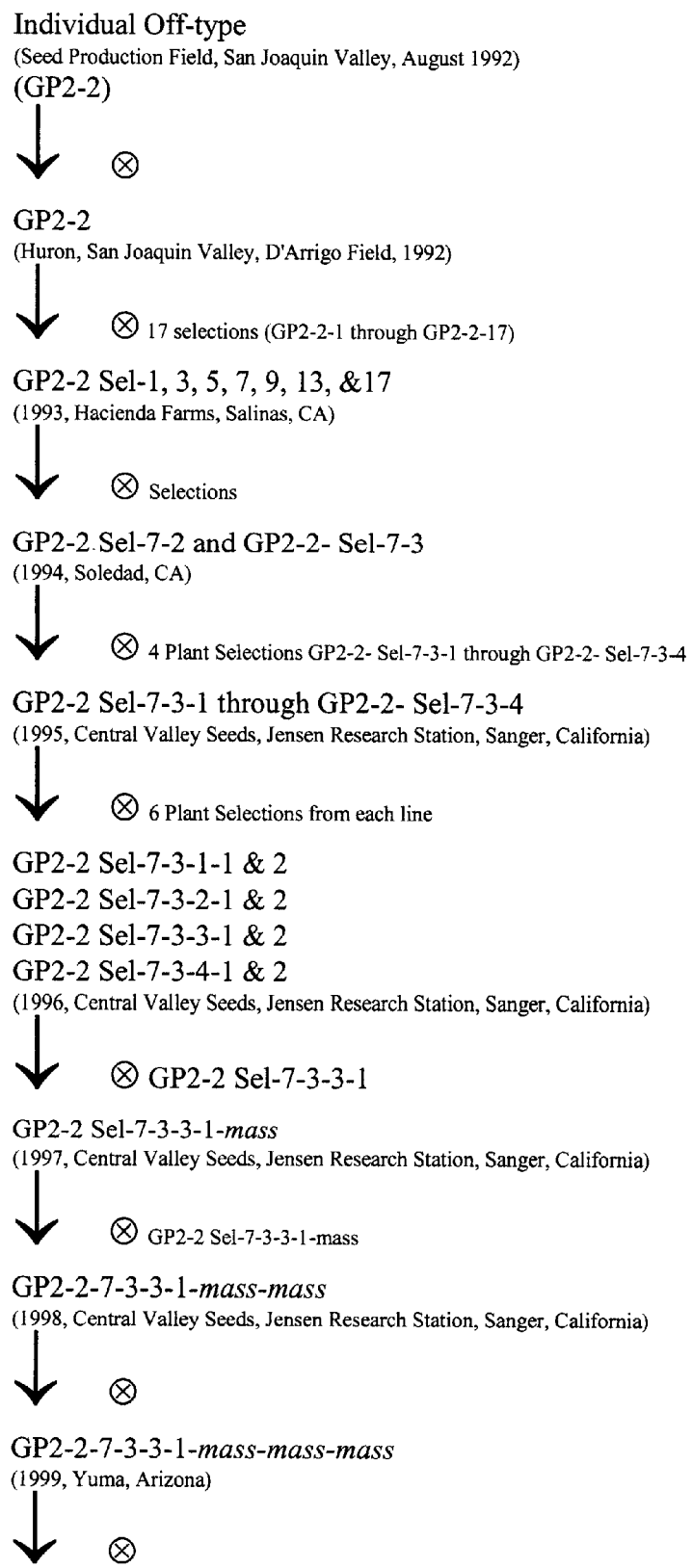

LACTUCA SATIVA CULTIVAR, 'THERMO COS', EXHIBITING RESISTANCE TO LETTUCE DROP (SCLEROTINIA MINOR) AND TIPBURN

BACKGROUND OF THE INVENTION

1. Field of the Invention

The present invention relates to a new distinct *Lactuca sativa* romaine cultivar that exhibits resistance to lettuce drop (*Sclerotinia minor*) and tipburn.

2. Background of the Invention

Vegetables and especially lettuce have growing importance in the human diet. There are unique qualities to these foodstuffs that make them critically important to good health and longevity of life. Such vegetables are nearly exclusive eaten in their natural state as a fresh, raw product. As such the appearance of such vegetables is critical to their sale. Americans especially demand a perfect or near perfect appearance of their raw food products. Whereas, in some countries, foodstuffs can have blemishes and imperfections and be fit for the market, the US consumer demands a perfect near unblemished product.

Additionally, Americans are very demanding of the color of their food. Various is shades of color can determine whether a food product is successful at market. A deeper shade of green looks more appetizing than a pale shade of green or a green with a yellowish tint. A deep green in a ripe, healthy head of lettuce is especially desirable in a romaine lettuce and its varieties and has been found to be especially strong commercially.

It will be appreciated that all growers are faced with a limited amount of space in which to grow their vegetables and food products. It is more than desirable to maximize the yield of a particular parcel and especially so for the small to moderate sized grower. For example, if a grower can break even by selling about 500 cartons of lettuce per acre and he can switch to a different variety of the same lettuce and grow about 900 cartons of lettuce per acre, the product of the different variety would be much more valuable. This very well could be the difference between a grower able to survive bad economic conditions one year and continue his operation or going under and being forced to sell out or turn his land in residential property. Intense heat is considerably unfavorable for production of fresh market lettuce. Due to severe sun injuries, i.e. tipburn and scorching, no fresh lettuce is produced during the very hot early to late summer months in the San Joaquin Valley.

The export of vegetables across the international and state lines is vital to the grower. In 1998, lettuce was fifth among California's top 20 crops with an estimated value of about $1.1 billion from 213,000 acres. In fact, California and Arizona grow about 90% of the total United States lettuce production and It is estimated that about 75% or more of all lettuce grown in California is so exported (Subbaroa 1998) for sale in states such as New York, Pennsylvania, Massachusetts and the like.

It is also traditional to export lettuce. Originally, lettuce was trucked from one location to another using ice to keep the lettuce fresh. This is how the name "iceberg" lettuce came into being. Thus, not only is lettuce exported from the growing regions, but it has been so in the past and is likely to being for many future years as well.

For a further understanding of lettuce, its uses and history Waycott et al, U.S. Pat. No. 5,973,232 and Subbaroa 1998 is incorporated herein by references. There are six morphological types of lettuce: crisphead (iceberg), butterhead, Cos (romaine), leaf, stem and Latin. The crisphead is the most common in the United States, while butterhead and romaine types are popular in northern and southern Europe. Id.

Lettuce originated from the ancestral wild species *L sativa*. Today there are over one hundred cultivars, which are divided in commerce into four large groups based on gross morphological characteristics of the gross leaf morphology and leaf arrangement (Subbaroa 1998). These basic lettuce types frequently form the basis for grouping lettuces as is commonly seen in supermarkets, grocery and produce stores. Each of these basic groups is comprised of numerous cultivars; each characterized by its own particular morphology, disease resistance, and cultural adaptations.

Lettuce cultivars are susceptible to a number of diseases such as downy mildew (*Bremia lactucae*), lettuce drop (*Scierotinia minor* and *S. scierotiorum*), corky root (*Rhizomonas suberifaciens*), lettuce mosaic virus, big vein, and aster yellows, just to list a few. These diseases result in millions of dollars of lost lettuce crop through the world every year. In California alone, the average seasonal losses by lettuce drop, caused by *Sclerotinia minor* or *Sclerotinia scierotiorum*, is about 15% and may reach to about 60% or higher with heavy economic losses at higher lettuce prices. Lettuce drop effects all types of lettuce. There is no effective means of controlling lettuce drop and breeding host resistance cultivars remains the only logical option to manage the epidemiology of the disease.

The market quality of lettuce may also be influenced by abiotic factors. Tipburn disorder is one example. Tipburn incidence in lettuce is characterized by the presence of necrotic lesions at or near the margins of rapidly expanding inner enclosing mature leaves (Ryder 1998). Tipburn reaction is possibly related to a deficiency in plant calcium transport system along with reduced transpiration due to inner leaf enclosure. Inefficient concentration of calcium in the margins of rapidly expanding leaves may lead to cell wall breakdown and the occurrence of large to small lesion formation (Collier and Tibbitts 1982, Barta & Tibbitts 2000). Depending on the severity of tipburn at market stage, the grower may be entitled to lower market price or loss of the entire crop. Development of tipburn injury symptoms may occur when the daytime temperature ranges from 32 to 40 C (Ryder 1998). Plants may exhibit considerable tipburn injury at or near the market stage especially when the inner mature leaves have completely enclosed or cupped in. Lettuce cultivars with resistance to tipburn are highly desired by the growers.

In order for lettuce to be fit to travel to other states, each head of lettuce must pass a vigorous inspection. A part of the inspection calls for the lettuce plants to be free of rot, decay or tipburn. Even a small amount of rot or tipburn can open the door to an infection for the entire shipment. Thus, not just the infected plant or plant(s) are banned from travel across state lines, but the entire lot of lettuce will be prohibited should evidence of such lettuce drop or tipburn be found.

In order to be commercially viable, a grower must then be able to produce a sufficient quantity of plants that are healthy and fit for travel. The yield of the grower's acreage will determine the grower's financial success and whether he can continue his operation in the face of rising competition and market driven demands.

What is therefore needed is a lettuce plant variety that allows the grower to maximize his yield and provide plants that are desirable to the consuming public. It is also desirable to provide the lettuce grower with a lettuce plant that not only maximizes his yield and extends the growing season into the hot summer months, but also yields a plant, which is fit for travel across interstate lines. And, it is desirable to provide the lettuce grower with a lettuce plant which generates strong consumer sales by having the sought after color and appearance.

SUMMARY OF THE INVENTION

It is a general object of this invention to provide a new distinct romaine *Lactuca sativa* cultivar, which increases yield to growers.

It is another object of this invention to provide a new distinct romaine *Lactuca sativa* cultivar, which not only increases yield but also provides a pleasing and commercially desirable dark green color.

It is another object of this invention to provide a new distinct romaine *Lactuca sativa* cultivar, which not only increases yield but also with superior resistance to tipburn.

It is another object of this invention to provide a new distinct romaine *Lactuca sativa* cultivar, which not only increases yield but also with superior resistance to lettuce drop caused by fungal agent *Sclerotinia minor*.

It is yet another object of this invention to provide a new distinct romaine *Lactuca sativa* cultivar, which not only increases yield but also has a wide core diameter with a smaller core length.

The present invention comprises a new distinct romaine *Lactuca sativa* cultivar herein 'Thermo Cos'. Thermo Cos exhibits increased resistance to lettuce drop and tipburn. In addition, 'Thermo Cos' has a leaf color of Value 4 Chroma 4 Hue 7.5GY according to the Munsell Color Chart for Plant Tissues. In average, mature market stage heads of 'Thermo Cos' weigh about 730 grams compared to 752 grams for the closest comparable variety, King Henry, Plant Variety Protection Pending Number: 9600323 which is commercially available from Progeny Advanced Genetics, Inc. Salinas, Calif., 93907. Seeds of 'Thermo Cos' have been deposited with a public depository agency the American Type Culture Collection (ATCC), 10801 University Boulevard, Manassas, Va. 20110-2209 under the Budapest treaty on Mar. 20, 2000 and have assigned Accession number PTA-2252.

The present invention relates to a *Lactuca sativa* plant produced by growing the seed of 'Thermo Cos' that has ATCC Accession No. PTA-2252. The present invention also relates to a *Lactuca sativa* plant that has all the physiological and morphological characteristics of a *Lactuca sativa* plant grown from seed from ATCC Accession No. PTA-2252.

Finally, the present invention relates to a hybrid *Lactuca sativa* plant having 'Thermo Cos' as a parent.

BRIEF DESCRIPTION OF THE DRAWING

FIG. 1 illustrates the pedigree of lettuce cultivar Thermo Cos

DETAILED DESCRIPTION OF THE INVENTION

Definitions

The following definitions will be helpful in the discussion of 'Thermo Cos' cultivar that follows.

Cotyledon. In the case of lettuce, one of a pair of leaves formed on an embryo within a seed, which upon germination are the first leaves to emerge.

Fourth Leaf. The fourth leaf formed on the lettuce plantlet subsequent to the emergence of the cotyledons.

Frame Leaf. The first set of freely recurring leaves which are external to the head.

Market Stage. The developmental stage reached by a crop plant at which time the plant is ready for market. In Iceberg Group cultivars of lettuce, it is that stage at which the head has reached a maximum size before bolting but in which most of the head leaves are still tightly clasping.

Butt. The bottom portion of the lettuce head which includes the stem and adjacent leaf bases of the outermost head leaves.

Core. The stem of the lettuce head on which the leaves are borne.

Bolt. The process during which the stem within the lettuce head greatly elongates, causing the head to lose its shape and resulting ultimately in the producing of a flowering stalk.

Origin and Parentage of 'Thermo Cos'

Referring now to FIG. 1, the genealogy of lettuce cultivar of the present invention, herein designated, as 'Thermo Cos' will now be described. 'Thermo Cos' is a Cos or romaine lettuce variety. 'Thermo Cos' was developed, in summer of 1992, from a single black-seeded plant growing in the middle of the white-seeded 'Oasis' crisphead seed production field of Central Valley Seeds, Inc. in San Joaquin Valley, Calif. The plant selection was utterly based on the presence of a black-seeded lettuce off-type with semi-romaine leaf structure growing among the white seeded crisphead seed production field. The selected plant was labeled as GP2-2 and was allowed to self-pollinate in the field and the resulting seeds were collected.

In August of 1992, approximately 60 plants of GP2-2 were grown in Huron, Calif. A number of crisphead types along with assortment of plants with variable shapes and leaf color, were observed. Seventeen romaine plants were individually selected for having dark green leaf color, extended plant height, thick and moderate savoy (blistering) leaves with slight leaf undulation and resistance to tipburn. The selected plants were labeled as GP2-2-1 through GP2-2-17 and were allowed to self-pollinate and the resulting seeds were collected. In the following year randomly 7 of the 17-selfed seed lines, GP2-2 Sel-1, 3, 5, 7, 9, 13, &17, were planted in a field trial located at Hacienda Farms, Salinas, Calif. Several lines were segregating for different plant type, leaf structure, and color. Consideration was mainly given to line GP2-2 Sel-7 for having plants with medium height displaying wide to medium frame composition, thick and moderate savoy (blistering) leaf texture, slight leaf undulation, dull (non-glossy) dark green leaf color, very short core length, no tipburn and with no losses to lettuce drop disease caused by fungus *Sclerotinia minor*. Instead of a straight upright leaf petioles, majority of the selected plants displayed a concaved butt shape with prominently raised midribs that was ascertained to be comparatively unmatched for a Cos type lettuce. Ten individual plants with the characteristics described were selected from line GP2-2 Sel-7 and were labeled as GP2-2 Sel-7-1 through GP2-2 Sel-7-10. All plants, except GP2-2 Sel-7-2 and 3, died after greenhouse transplanting. The remaining two plant selections were allowed to self-pollinate and the resulting seeds were collected.

Seeds of the lines GP2-2 Sel-7-2 and 3 were planted in Central Valley Seeds' research station, Soledad, Calif. Line GP2-2 Sel-7-2 was profoundly segregating and was drop from further evaluation and selection. However, four individual plants were selected from line GP2-2 Sel-7-3. These plants displayed wide to medium frame structure, thick and moderate savoy (blistering) leaf texture, slight leaf undulation, dull (non-glossy) dark green leaf color, very short core length, no tipburn with slight internal cupping, and a concaved butt shape with prominently raised midribs. Selections were labeled as GP2-2 Sel-7-3-1 through GP2-2 Sel-7-3-4 and were allowed to self-pollinate and the resulting seeds were collected.

Intense heat is considered unfavorable for production of fresh market lettuce. Due to severe sun injuries, i.e. tipburn, scorching or leaf twisting, no fresh market lettuce is produced during the very hot summer months in the San Joaquin Valley, Calif. No adverse reaction to tipburn or scorching had been noticed during the field observation and selection of the plants. For the extent of tipburn resistance and other heat related injuries, in 1995 a decision was made to conduct future field evaluations and plant selections under extreme heat in the Central Valley Seeds' Jensen Research station in Sanger, Calif. Individual plants from lines GP2-2 Sel-7-3-1 through GP2-2 Sel-7-3-4 were appeared to possess the described selection criteria and were emerging to be genetically stable. In addition, tipburn, scorching and leaf twisting caused by excess heat were markedly absent. Therefore, from each line, six individual plants were selected and were labeled accordingly. The plants were allowed to self-pollinate and the resulting seeds were collected.

Since the lines were appeared to be genetically stable, only the first two seed lines from each selection were evaluated in 1996. Other than expected minor variances due to the environmental factors, it was evident that all of the selected lines were judged to be genetically stable and uniform. Plants in line GP2-2 Sel-7-3-3-1 appeared to possess the most uniformity and displayed wide to medium frame structure, thick and slightly savoy (blistering) leaf texture, moderate leaf undulation, dull (non-glossy) dark green leaf color, very short core length, no tipburn or scorching, slight internal cupping, and a concaved butt shape with prominently raised midribs. No further individual plant selection was made. The entire GP2-2 Sel-7-3-3-1 line was massed together and was allowed to self-pollinate and the resulting seeds were collected.

Field performance of the resulting massed seeds was re-evaluated in the 1997 trial. Line GP2-2 Sel-7-3-3-1-mass displayed the uniformity and stability for all the traits described. The entire GP2-2 Sel-7-3-3-1-mass line was labeled as GP2-2 Sel-7-3-3-1-mass-mass and was massed together for another generation. The plants were allowed to self-pollinate and the resulting seeds were collected.

In summer of 1998 seed line GP2-2 Sel-7-3-3-1-mass-mass was re-evaluated in Central Valley Seeds' Jensen Research station in Sanger, Calif. The resulting plants shown the uniformity and stability for wide to medium frame structure, thick and slightly savoy (blistering) leaf texture, moderate leaf undulation, dull (non-glossy) dark green leaf color, very short core length, no tipburn or scorching, slight internal cupping, and a concaved butt shape with prominently raised midribs. Plants from the entire line were collectively massed as GP2-2 Sel-7-3-3-1-mass-mass-mass and were allowed to self-pollinate and the resulting seeds were collected.

In 1999, the line GP2-2 Sel-7-3-3-1-mass-mass-mass was re-evaluated in Yuma, Ariz. Plants performed exceptionally well and displayed the uniformity and stability for all the traits described. The experimental designated breeding line GP2-2 Sel-7-3-3-1-mass-mass-mass was given the name Thermo Cos for its outstanding performance under extreme heat. 'Thermo Cos' has been suggested for commercial planting as a Cos or romaine cultivar in the warm regions of California and Arizona. Compared to other romaine varieties, 'Thermo Cos' is unique for its class and is relatively medium in height, with a medium frame structure, thick and slightly savoy (blistering) leaf texture, moderate leaf undulation, dull dark green leaf color, very short core length, no tipburn or scorching, slight internal cupping, and a concaved butt shape with prominently raised midribs. Interior leaves of other romaine varieties may be yellowish while 'Thermo Cos' comparatively maintains its non-glossy dark green leaf color down to its interior small or baby leaves. Depending on the planting space and modified cultural practices, 'Thermo Cos' can be grown for hearts or for fresh market lettuce approximately at 8 or 10 inch spacing, respectively.

'Thermo Cos' lettuce variety is distinct, genetically stable and uniform. After eight generations no variants or off types, other than what would normally be expected due to environment or that would occur for almost any biological character during the course of repeated sexual reproduction, have been observed in commercial fields or the seed production trials. Therefore, the combination of traits disclosed herein that characterizes the new lettuce variety 'Thermo Cos' are fixed and are attentively retained true to type through successive generations of sexual reproduction. Seeds of 'Thermo Cos' have been deposited with a public depository agency the American Type Culture Collection (ATCC), 10801 University Boulevard, Manassas, Va. 20110-2209 under the Budapest treaty on Mar. 20, 2000 and have assigned Accession number PTA-2252. Compared to the available commercial romaine varieties, 'Thermo Cos' is highly resistant to lettuce drop disease caused by Sclerotinia minor and shows very high degree of resistance to tipburn particularly several days past its market stage. Plants were evaluated based on visible lettuce drop symptoms. Symptoms may include rapid plant wilt, decay, and dying or complete death of the plant. Plants were considered dead when the entire plant has collapsed or dying when the outermost leaves appeared yellow in color and in the process of wilting. The presence of watery fungal decay at the crown or basal portion of the plant confirmed the presence of *S. minor* as the causal agent of lettuce drop in each test plot evaluation. Rating for resistance or susceptibility was based on the percentage of survived harvestable and marketable disease-free plants. In all test plots, the 'Thermo Cos' was grown side by side of the commercially planted variety(s), which was used as a control. Depending on the planting space and modified cultural practices, 'Thermo Cos' can be grown for hearts or fresh market at 8 or 10 inch spacing, respectively.

'Thermo Cos' lettuce variety is distinct, genetically stable and uniform. After eight generations no variants or off types have been observed in commercial fields or the seed production trials.

Additionally, 'Thermo Cos' is sweeter in taste and flavor compared to the available commercial varieties.

Comparison to the Closest Variety

EXAMPLE 1

'Thermo Cos' is almost similar to the lettuce romaine variety King Henry but is distinguished by the following general phenotypic characteristics listed in Table 1.

TABLE 1

| Area | 'Thermo Cos' | King Henry |
| --- | --- | --- |
| Leaf Blistering (Savoyedness) | Slight | Moderate |
| Plant Height | Medium | Tall |
| Leaf Glossiness | Dull (non-glossy) | Semi-glossy |
| *Leaf Color | Dark Green | Light Green |
| Corky Root | Intermediate | Resistant |
| Maturity | About 2–3 Days Late | About 2–3 Days Early |

*According to the Munsell Color Chart for Plant Tissues, Thermo Cos has Value 4 Chroma 4 Hue 7.5 GY and King Henry has value 4 Chroma 8 Hue 5 GY.

EXAMPLE 2

'Thermo Cos' and 'King Henry' differ from one another in leaf width, leaf length, core diameter, core volume, leaf shape, and tipburn resistance (Tables 2 and 3).

'Thermo Cos' is most similar to 'King Henry'; however, 'Thermo Cos' has wider leaves (cm) than King Henry at the market stage.

'Thermo Cos' is most similar to 'King Henry'; however, 'Thermo Cos' has longer leaves (cm) than 'King Henry' at the market stage.

'Thermo Cos' is most similar to 'King Henry', however, 'Thermo Cos' has larger core diameter than 'King Henry' at the market stage.

'Thermo Cos' is most similar to 'King Henry'; however, 'Thermo Cos' has larger core volume index than 'King Henry' at the market stage.

'Thermo Cos' is most similar to 'King Henry'; however, 'Thermo Cos' leaf index is significantly different than 'King Henry'. In other words, 'Thermo Cos' has a different leaf shape, in relation to the width and length, than 'King Henry'.

'Thermo Cos' is most similar to 'King Henry'; however, at the market stage, 'Thermo Cos' has wider, longer leaves; a larger core diameter; a larger core volume index than 'King Henry' and is more highly resistant to tipburn.

TABLE 2

| Trial[a] Locations | Variable[b] | $t^*$-Value | $p[t^*]$ | Avg. 'Thermo Cos' | Avg. 'King Henry' | Sigma | LSD Mean 95% |
| --- | --- | --- | --- | --- | --- | --- | --- |
| 1 | Leaf Width (cm) | 3.76 | 0.001 | 21.4 | 19.3 | 1.23 | 1.15 |
| 2 | Leaf Width (cm) | 3.55 | 0.002 | 21.5 | 19.5 | 1.24 | 1.16 |
| 1 | Leaf Length (cm) | 2.57 | 0.019 | 28.6 | 26.8 | 1.52 | 1.43 |
| 2 | Leaf Length (cm) | 2.75 | 0.013 | 29.0 | 27.1 | 1.58 | 1.49 |
| 1 | Core Diameter (cm) | 4.3 | 0.000 | 4.9 | 4.3 | 0.38 | 0.29 |
| 2 | Core Diameter (cm) | 3.6 | 0.002 | 5.0 | 4.3 | 0.40 | 0.37 |
| 1 | Core Volume Index[c] | 2.57 | 0.019 | 156.0 | 126.9 | 25.2 | 23.6 |
| 2 | Core Volume Index[c] | 2.35 | 0.030 | 169.5 | 136.2 | 31.5 | 29.6 |
| 1 | Leaf Area Index[d] | 4.14 | 0.001 | 612.0 | 519.0 | 50.2 | 47.1 |
| 2 | Leaf Area Index[d] | 3.95 | 0.001 | 625.4 | 530.0 | 53.9 | 50.7 |

[a]Field Trial Locations:
Location 1: D'Arrigo Brothers, Ranch # 10, lot # 40, Greenfield, California. Water Date: May 3, 2000. Evaluation Date: Jul. 7, 2000.
Location 2: D'Arrigo Brothers, Ranch # 11, lot # 21, Soledad, California. Water Date: May 11, 2000. Evaluation Date: Jul. 17, 2000.
No. of reps: 10 plants per entry per trial.
[b]Measurements in centimeters taken at market stage.
[c]The core volume index is calculated by taking the core length multiplied by the core diameter$^2$.
[d]The leaf area index compares the total leaf areas between the two varieties. This is calculated by multiplying the leaf width by the leaf length.

TABLE 3

| [a]Trial Location | No. Plants Per Rep | [b]No. Tipburn 'Thermo Cos' | No. Tipburn 'King Henry' | [c]p [Chi sq.] |
| --- | --- | --- | --- | --- |
| 1 | 25 | 0 | 6 | 0.014 |
| 2 | 25 | 0 | 5 | 0.025 |
| 3 | 25 | 0 | 4 | 0.045 |

[a]Field Trial Locations:
Location 1: D'Arrigo Brothers, Ranch # 10, lot # 40, Greenfield, California. Water Date: May. 3, 2000. Evaluation Date: Jul. 7, 2000.
Location 2: D'Arrigo Brothers, Ranch # 11, lot # 21, Soledad, California. Water Date: May. 11, 2000. Evaluation Date: Jul. 17, 2000.
Location 3: D'Arrigo Brothers, Ranch # 14, lot # 13, Chular, California. Water Date: May. 18, 2000. Evaluation Date: Jul. 25, 2000.
[b]presence or absence of plants with tipburn symptoms was recorded as 1 and 0, respectively.
[c]Statistical analysis based on the probability of one-tailed Chi-squared distribution at 95% level.

EXAMPLE 3

Variety Description Information

The romaine lettuce, *Lactuca sativa*, cultivar 'Thermo Cos' has the following morphologic and characteristics:

1.0 Plant Type: Cos or Romaine
2.0 Seed
   Seed Color: black (gray brown)
   Light Dormancy: Light is not required
   Heat Dormancy: Not susceptible
3.0 Cotyledons
   Shape of Cotyledons: Broad
   Shape of Fourth Leaf: Elongated Cos type
   Length/Width Index of Fourth Leaf: (L/W.times.10)=
   Apical Margin: Entire
   Basal Margin: Coarsely Dentate
   Undulation: Slight
   Green Color: Dark Green
   Anthocyanin:
   Distribution: Absent
   Rolling: Absent Cupping: Slight
Reflexing: None
4.0 Mature Leaves
  Margin:
    Incision Depth (Deepest penetration of the margin): absent/shallow (like Parris Island Cos which is commercially available from Central Valley Seeds, Inc., Salinas, Calif. 93907).
    Indentation (Finest Division of the Margin): Entire (like Dark Green Boston which is available from the United States Department of Agriculture ARS, 1636 East Alisal Street, Salinas, Calif. 93905).
    Undulation of the Apical Margin: Absent/Slight (like Dark Green Boston)
  Green Color: Dark Green (Vanguard)
  Anthocyanin (Grown at or below 10.degree. C.):
    Distribution: Absent
    Size: Medium
    Glossiness: Dull (Vanguard—Seed of Vanguard is available from the United State Department of Agriculture, ARS, 1636 East Alisal Street, Salinas, Calif. 93905).
    Blistering: Moderate (Vanguard—Seed of Salinas is available from the United States Department of Agriculture, ARS, 1636 East Alisal Street, Salinas, Calif. 93905).
  Leaf Thickness: Thick
  Trichomes: Absent (Smooth)
5.0 Plant
  'Thermo Cos' Spread of Frame Leaves: 20 cm
  'King Henry' (comparison variety): 18 cm
  Head Shape: Non-Heading
  Head Size Class:
  Head Count per Carton: 24
  Head Weight:
    'Thermo Cos': 730 g
    'King Henry': 752 g
  Head Firmness: Loose
6.0 Butt: (Bottom of Market-trimmed Head)
  Shape: Slightly Concave
  Midrib: Prominently Raised (Great Lakes 659)
7.0 Core (Stem of Market-trimmed Head):
  Diameter at the base of the Head: 45 mm
  Ratio of Head Diameter/Core Diameter:
  Core Height from base of Head to Apex
    'Thermo Cos': 69 mm
    'King Henry' (comparison variety): 69 mm
8.0 Bolting—First Water Date May 20, 1996.
  (Note: The first water date is the date the seed first receives adequate moisture to germinate. This can and often does equal the planting date).
  Number of Days from First Water Date to Seed Stalk Emergence (Summer condition):
    Thermo Cos: 79 days
    King Henry: N/A days
  Bolting Class: Slow
  Height of Mature Seed Stalk:
    'Thermo Cos': 102 cm
    'King Henry' (comparison variety): N/A cm
  Spread of Bolter Plant:
    'Thermo Cos': 37 cm
    'King Henry' (comparison variety): N/A cm
  Bolter Leaves: Curved
  Margin: Entire
  Color: Dark Green
  Bolter Habit
  Terminal Inflorescence: Absent
  Lateral Shoots (above head): Absent
  Basal Side Shoots: Absent
9.0 Maturity (earliness of harvest-mature head formation):

| Season Application ('Thermo Cos') from # of days* .sup.1 | | Check ('King Henry') # of Days* .sup.1 |
|---|---|---|
| Spring | N/A | N/A |
| Summer | 63 | 65 |
| Fall | 65 | 69 |
| Winter | N/A | N/A |
| Planting Dates and Locations | | |
| Spring | N/A | |
| Summer | May 18, Chular, California | |
| Fall | September 16, Yuma, Arizona | |
| Winter | N/A | |

*.sup.1 First water date to harvest.

10.0 Adaptation
  Primary Regions of Adaptation (tested and proven adapted):
    Southwest (California, Arizona desert): Adapted
    Southeast: Not tested
    West Coast: Adapted
    Northeast: Not tested
    Northcentral: Not tested
    Southeast: Not tested
  Season
    Spring area-Yuma, Ariz.
    Summer area—Salinas Valley, Coastal California
    Fall area—Yuma, Ariz., Imperial Valley, Calif.
    Winter Area—Not tested
    Greenhouse: Not tested
  Soil Type: Mineral
11.0 Diseases and Stress Reactions
  Big Vein: Intermediate
  Lettuce Mosaic: Susceptible
  Cucumber Mosaic: Not tested
  Broad Bean Wilt: Not tested
  Turnip Mosaic: Not tested
  Beet Western Yellows: Not tested
  Lettuce Infectious Yellows: Not tested
  Fungal/Bacterial
  Corky Root Rot (Pythium Root Rot): Not tested
  Downy Mildew (Races IIA, IIB, III, V): Susceptible
  Powdery Mildew: Not tested
  Sclerotinia Rot: Highly resistant
  Bacterial Soft Rot (Pseudomonas spp. & others): Not tested
  Botrytis (Gray Mold): Not tested
  Corky root (*Rhizomonas suberifaciens*): Susceptible
  Insects
  Cabbage Loopers: Not tested Root Aphids: Not tested
Green Peach Aphid: Susceptible
Physiological/Stress
Tipburn: Highly resistant
Heat: Highly resistant
Drought: Not tested
Cold: Intermediate
Salt: Not tested
Brown Rib (Rib Discoloration, Rib Blight): Resistant
Post Harvest
Pink Rib: Resistant
Russet Spotting: Not tested
Rusty Brown Discoloration: Not tested
Internal Rib Necrosis (Blackheart, Gray Rib, Gray Streak): Not tested
Brown Stain: Not tested Deposit of Thermo Cos Seeds of 'Thermo Cos' have been deposited with the American Type Culture Collection (ATCC), 10801 University Boulevard, Manassas, Va. 20110-2209. The deposit was made on Mar. 20, 2000 and received ATCC accession number PTA-2252.

Although the cultivar of the forgoing invention has been described and illustrated, it should be understood that certain changes and modifications may be practiced within the scope of this invention without departing from the scope of the invention as set forth in the accompanying claims. All restrictions upon availability to the public of the deposit made to ATCC of the above identified plant will be irrevocably removed upon the granting of the patent.

While the foregoing detailed description has described several embodiments of the plant variety in accordance with this invention, it is to be understood that the above description is illustrative only and not limiting of the disclosed invention. Particularly, a range of dark green color is considered within the spirit and scope of the invention. Additionally, a range of resistance to both lettuce drop (*Sclerotinia minor*) and tipburn is also considered within the range of patentable subject matter that is also considered to within the spirit and scope of this invention. It will be appreciated that the embodiments discussed above and the virtually infinite embodiments that are not mentioned could easily be within the scope and spirit of this invention. Thus, the invention is to be limited only by the claims as set forth below.

REFERENCES

Barta, D. J. and T. Tibbitts (2000). Calcium Localization and Tipburn Development In Lettuce Leaves During Early Enlargement. J. Amer. Hort. Sci. 125(3):294–298.

Collier, G. F. and T. Tibbitts (1982). Tipburn of Lettuce. Hort. Rev. 4:49–65.

Munsell Color Chart for Plant Tissues (1968). $2^{nd}$ Edition. Munsell Color Company, Inc. Baltimore, Md., USA.

Ryder, E. J and W. Waycot (1988). Crisphead Lettuce Resistant to Tipburn: Cultivar Tiber And Eight Breeding Lines. Hortscience 33(5): 903–904.

Subbarao, K. V. (1988) Progress Toward Integrated Management of Lettuce Drop. Plant Disease 82(10) 1068–1078.

What is claimed is:

1. *Lactuca sativa* seed designated as 'Thermo Cos' having ATCC Accession No. PTA-2252.

2. A *Lactuca sativa* plant produced by growing the seed of claim 1.

3. A *Lactuca sativa* plant having all the physiological and morphological characteristics of the *Lactuca sativa* plant of claim 2.

4. Propagation material of the plant of claim 1.

5. Pollen of the plant of claim 1.

6. Seeds of the plant of claim 1.

7. A method for producing a hybrid *Lactuca sativa* plant, said method comprising crossing the *Lactuca sativa* plant of claim 2 or claim 3 with a different *Lactuca sativa* plant.

* * * * *